(12) United States Patent
Jones (10) Patent No.: US 9,658,058 B1
(45) Date of Patent: May 23, 2017

(54) HEIGHT MEASURING DEVICE

(71) Applicant: Mark Conrad Jones, Austin, TX (US)

(72) Inventor: Mark Conrad Jones, Austin, TX (US)

(*) Notice: Subject to any disclaimer, the term of this patent is extended or adjusted under 35 U.S.C. 154(b) by 0 days.

(21) Appl. No.: 15/019,944

(22) Filed: Feb. 9, 2016

(51) Int. Cl.
*G01B 3/10* (2006.01)
*G01B 11/06* (2006.01)

(52) U.S. Cl.
CPC ........ *G01B 11/0608* (2013.01); *G01B 3/1084* (2013.01)

(58) Field of Classification Search
CPC .............................. G01B 5/00; G01B 5/0035
USPC ..................................... 33/511, 512
See application file for complete search history.

(56) References Cited

U.S. PATENT DOCUMENTS

| | | | |
|---|---|---|---|
| 4,896,432 A * | 1/1990 | Kang | A61B 5/1072 33/768 |
| 5,499,457 A * | 3/1996 | Weiler | A61B 5/1072 33/512 |
| 6,073,359 A | 6/2000 | Lee | |
| 6,163,971 A * | 12/2000 | Humphries, Jr. | A61B 5/1074 33/512 |
| 6,226,881 B1 | 5/2001 | Landauer | |
| 6,237,239 B1 * | 5/2001 | Miyazaki | A61B 5/1072 33/512 |
| 6,256,896 B1 * | 7/2001 | Landauer | A61B 5/107 33/512 |
| 7,987,612 B2 | 8/2011 | Hong | |
| 8,015,723 B2 | 9/2011 | Solomon | |
| 8,539,690 B2 | 9/2013 | Haykeen | |
| 8,869,415 B1 | 10/2014 | Haykeen | |
| 2003/0159300 A1 * | 8/2003 | Moss | G01B 5/061 33/512 |
| 2005/0210694 A1 * | 9/2005 | Leyden | A61B 5/1072 33/492 |
| 2010/0179767 A1 * | 7/2010 | Goldman | G01B 5/0035 702/19 |
| 2011/0179663 A1 * | 7/2011 | Kang | A61B 5/1072 33/759 |
| 2013/0158364 A1 * | 6/2013 | Hayn | A61B 5/1116 600/301 |

* cited by examiner

*Primary Examiner* — Yaritza Guadalupe-McCall (57) ABSTRACT

An apparatus, system and method for measuring height of one or more objects/users. Once the height measuring device is calibrated, a retracting foot platform is positioned atop a user/object and its distance is captured, stored and calculated by a distance sensor to determine the resulting heights of the objects/users. The distance sensors may come in the form of a linear encoder or a rotary encoder. The height measurements may be displayed on a screen, including the screen display of the height measuring device itself, or other devices such as a tablet, smartphone or scale. The height data from each user/object may be compared to one another. The height measuring device also includes a predictive algorithm that determines the future height of one or more users.

12 Claims, 7 Drawing Sheets

HEIGHT MEASURING DEVICE

CROSS-REFERENCE TO RELATED APPLICATION

The present application is related to U.S. patent application also entitled "Height Measuring Device" filed simultaneously. This application is related by subject matter to that disclosed in the commonly owned, and simultaneously-filed application.

BACKGROUND

Field of the Disclosure

This invention relates to an apparatus and method for measuring height.

Background of the Disclosure

Height measurement devices have evolved over the years. Traditionally, a person's height is either taken with a limp tape measure at home or at the doctor's office using a bulky, oversized height scale, typically having a floor base. Other wall mounted devices use a long cumbersome graduated rod having a sliding plank, or a basic graduated retractable tape having a hard to read parallax sight, and a plank.

Several additional electronic measurement devices have been introduced over the past decades to capture height. Some devices electronically capture the vertical position of a person and report the corresponding height measurement, by physically placing a device on top of a person's head, calculating the person's height by measuring the distance from the floor to the ceiling, and then subtracting the distance from the person's head to the ceiling. However, this requires a clear line of sight to a non-vaulted ceiling, and a floor. Due to the ability of the device sliding off the person's head, it has a higher probability of improperly calculating the person's height.

However, this current height-measuring device provides more stability by being mounted onto a surface, not balancing atop of a user's head, and not needing to be located at a prescribed distance from the floor. Further, it does not rely on a bulky floor base apparatus to measure height and there is no parallax error in the reading of its measurements. It provides for a more efficient and accurate height measurement through the incorporation of a distance sensor that calculates heights via the difference of a calibration reading from a distance reading, and it is triggered when a foot platform is moved to a different position. The distance sensor may include a linear encoder or a rotary encoder.

BRIEF SUMMARY

An apparatus, method, and system for measuring height are provided. The apparatus, and method includes initiating, and calibrating a height-measuring device, by engaging a distance sensor to capture and store the calibration reading. The distance sensor may be in the form of a rotary encoder or a linear encoder. A foot platform, connected to a retractable tape, is pulled atop an object/user. A reading is captured and is used as the distance reading. The distance sensor captures, stores, and calculates a height measurement for the user/object, and displays the height measurement on a screen. and calculates a height measurement for the user/object, and displays the height measurement on a screen. and calculates a height measurement for the user/object, and displays the height measurement on a screen.

The system includes processor instructions that are capable of capturing, calculating, and storing calibration data as well as height measuring data for one or more objects, including users. It then displays calculated height results of the objects/users. Further, the height data can be compared for more than one object/user. The height data may also be processed using a predictive algorithm in order to predict future height of one or more user or object. The height measurements, including compared heights, and predicted heights may be stored, and displayed on any plurality of screens, including smartphones, scales, tablets, and the like. The height measurements, including compared heights, and predicted heights may be stored, and displayed on any plurality of screens, including smartphones, scales, tablets, and the like. The height measurements, including compared heights, and predicted heights may be stored, and displayed on any plurality of screens, including smartphones, scales, tablets, and the like.

This summary is provided to introduce a selection of concepts in a simplified form that are further described in the detailed description. This summary is not intended to identify key features or essential features of the claimed subject matter, nor is it intended to be used to limit the scope of the claimed subject matter.

BRIEF DESCRIPTION OF THE DRAWINGS

The invention is illustrated by the following non-limiting drawings in which.

DETAILED DESCRIPTION

Figure 1:
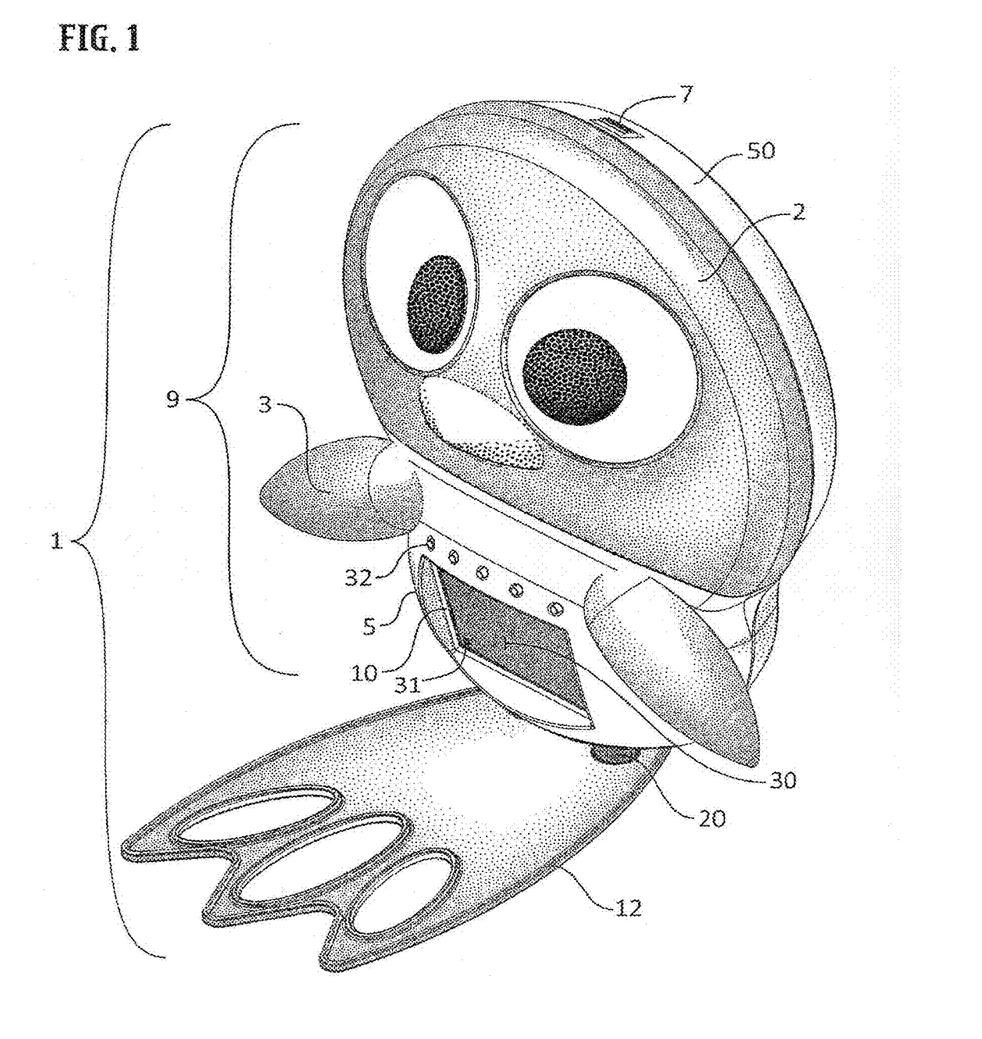
FIG. 1 is a front perspective view of a height-measuring device.

FIG. 1 depicts a height-measuring device [1] comprising a housing having a front shell assembly [9] and corresponding rear-facing shell [50]. The front shell assembly [9] in the preferred decorative embodiment includes a head [2] having a molded snap tab [7], a belly [5] having a display aperture [10], a screen display [30] having an integrated camera [31], at least one manual pushbutton [32], and decorative arms [3]. However, the front shell assembly [9] is not limited to having any decorative façade features and may be purely functional in design. The foot platform [12] perpendicularly abuts the underside of the belly [5] and the bottom of the rear-facing shell [50] of the housing. The foot platform [12] preferably includes one or more bumpers [20] to prevent the foot platform [12] from directly contacting and damaging the underside of the housing. The foot platform [12] may include a decorative design, such as molded toe cutouts to heighten user experience.

Figure 2:
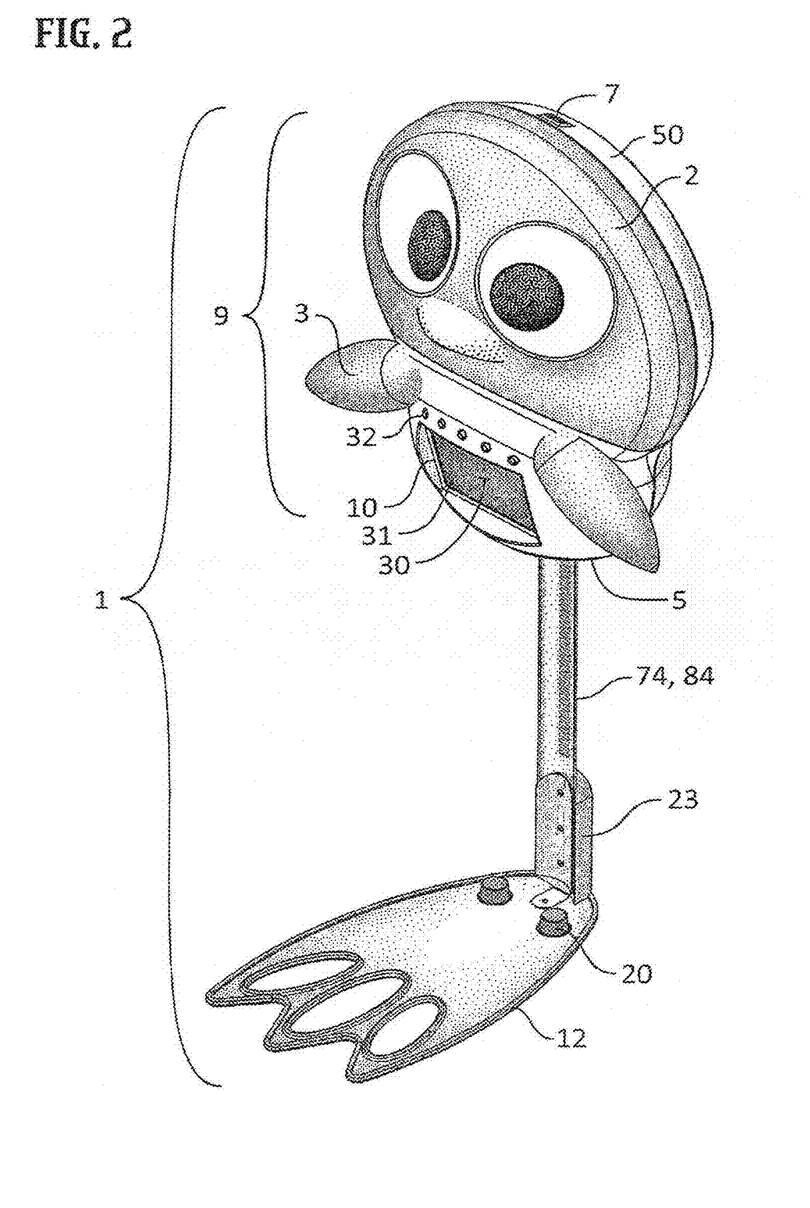
FIG. 2 is an isometric view of the height-measuring device with the foot in an extended position.

FIG. 2. depicts the height-measuring device [1] with the foot platform [12] in a partially extended position. The foot platform [12] is connected to a coded retractable tape [74]/slotted retractable tape [84] and is affixed by a foot bracket [23] or other attachment. In a preferred embodiment the coded retractable tape [74]/slotted retractable tape [84]

have similar form and structure to that of a spring-loaded tape measure. similar form and structure to that of a spring-loaded tape measure.

Figure 3:
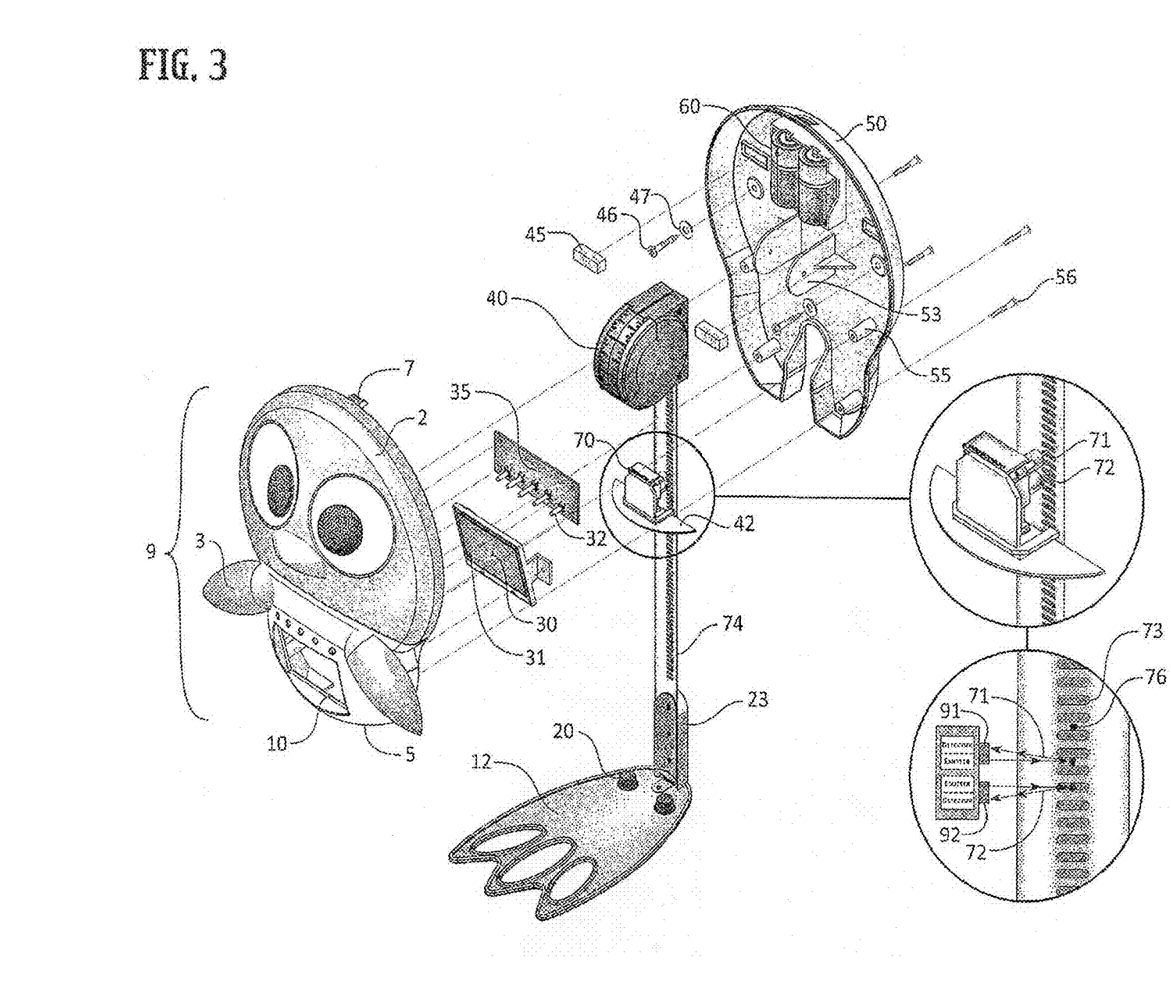
FIG. 3 is an exploded view of the height-measuring device having a linear encoder sensor.

FIG. 3 is an exploded view of the height-measuring device [1] of its linear encoder device embodiment, wherein a linear encoder laser device [70] is fixed onto a sensor bracket [42]. The linear encoder [70] has two adjacently protruding cylinder-shaped modules ([91], [92]), each having an emitter and detector pair. However, the linear encoder's [70] actual form factor, dimension, and assembled position may vary. The coded retractable tape [74] is made from thin, rigid, but flexible material, and is preferably contained within a spring loaded tape housing [40]. In order to hold the tape housing [40] into place, it is inserted between walls [53], which protrude perpendicularly from the rear-facing shell [50]. When the foot platform [12] is pulled down vertically, the coded retractable tape [74] synchronously travels downward while the remaining length of the coded retractable tape [74] remains in a coiled state within the spring loaded tape housing [40]. As the retractable tape [15] extends, it exits from the tape housing [40], becoming uncoiled, and passes through a partially surrounding sensor bracket [42], which keeps the coded retractable tape [74] confined within a certain clearance. The coded retractable tape [74] and foot bracket [23] provide vertical parallelism and horizontal rigidity of the foot platform [12] along its travel path. The rear-facing shell [50] is configured to be mountable onto a surface, such as a wall, using mounting screws [46] and washers [47]. Bubble type or electronic level indicator [45] may be affixed within the housing, preferably onto the interior of the rear-facing shell [50], to ensure the height-measuring device [1] has the truest perpendicular wall mount with respect to the floor. The rear-facing shell [50] may attach to the front shell assembly [9] using one or more fasteners [56] through molded bosses [55]. The head [2] section attaches, or detaches, by means of one or more molded snap tabs [7], providing for a non-fastener access to the power supply/battery [60], as well as convenient access to the mounting screws [46] of the height-measuring device [1] itself.

A screen display [30] having an integrated camera [31] is incorporated into the front shell assembly [9] and is positioned adjacent to a corresponding Application Specific Integrated Circuit (ASIC) board [35]. The ASIC board [35] houses system hardware such as manual pushbuttons [32], processors, wireless radios, memory modules, voice recognition modules, face recognition modules, camera modules, microphones, audio speakers, and other electronics and microelectronics. Along with the manual pushbuttons [32], the screen display [30] may be used as a touch screen that enables the user to press buttons, add information, and/or manipulate objects using Graphic User Interface (GUI) buttons on the screen display [30]. Camera [31] may be used for face recognition and/or user or object photographs. The height-measuring device [1] software accepts user inputs and/or object information, such as individual, or family member assignment, and can send data to the corresponding LED, LCD or similar screen display [30]. These options allow the user to easily input, initiate, manipulate, and/or associate user/object information, and password functionality.

The linear encoder [70] decodes height measurements of users or objects by using a set of two coordinated emitter beam ([71], [72]) signals, being 90° out-of-phase, projected onto a coded retractable tape [74] with a reflective surface, having an array of non-reflective, opaque segments [73] which are equidistantly spaced onto the coded retractable tape [74]. Each opaque segment [73] has a certain height and width, depicted here as, but not limited to 2-mm×10-mm, and the reflective zones [76] betwixt are equivalently spaced at a 2-mm distribution over the length of the coded retractable tape [74]. The specificity of size, and spacing of these opaque segments [73] and reflective zones [76] determines the linear encoder's [70] resolution. Note that from henceforth, the opaque segments [73] and reflective zones [76], being associated with a coded retractable tape [74] may be referenced as coded-media.

In operation, the coded-media travels downward until the adjoined foot platform [12] comes to its final rest atop the user's head or other object. Concurrent with this coded-media motion, both of the linear encoder's [70] emitter beams [71, 72] independently fire, and progressively scan over the array of opaque segments [73] and the reflective zones [76]. Meanwhile, the two respective detectors read, log, and cache the data as two channels of Square Wave Pulses (SWP) that are 90° out-of-phase. The first SWP channel is in-phase and may be used for electronic pulse counting, i.e. used in the distance measurement calculation process: while the second SWP channel is quadrature which may also be used for counting, but is preferably used in conjunction with the in-phase channel to detect instantaneous direction changes of the coded media. Effectively, electronic pulses are counted and the linear encoder's [70] processor calculates the coded media's incremental travel distance by multiplying the electronic pulses times the millimeters travelled per electronic pulse. In brief, the linear encoder [70] optionally employs one or both channels to increment and/or decrement electronic pulse counts; and, it necessarily employs both channels with quadrature evaluation to detect encoder media direction changes. The foregoing process incrementally aggregates the linear travel distance of the coded retractable tape [74] and the adjoined foot platform [12] during motion. Technologically, the linear encoder [70] heretofore mentioned is of the reflective-type but may also be transmissive, given some minor modifications of the apparatus depicted.

Figure 4:
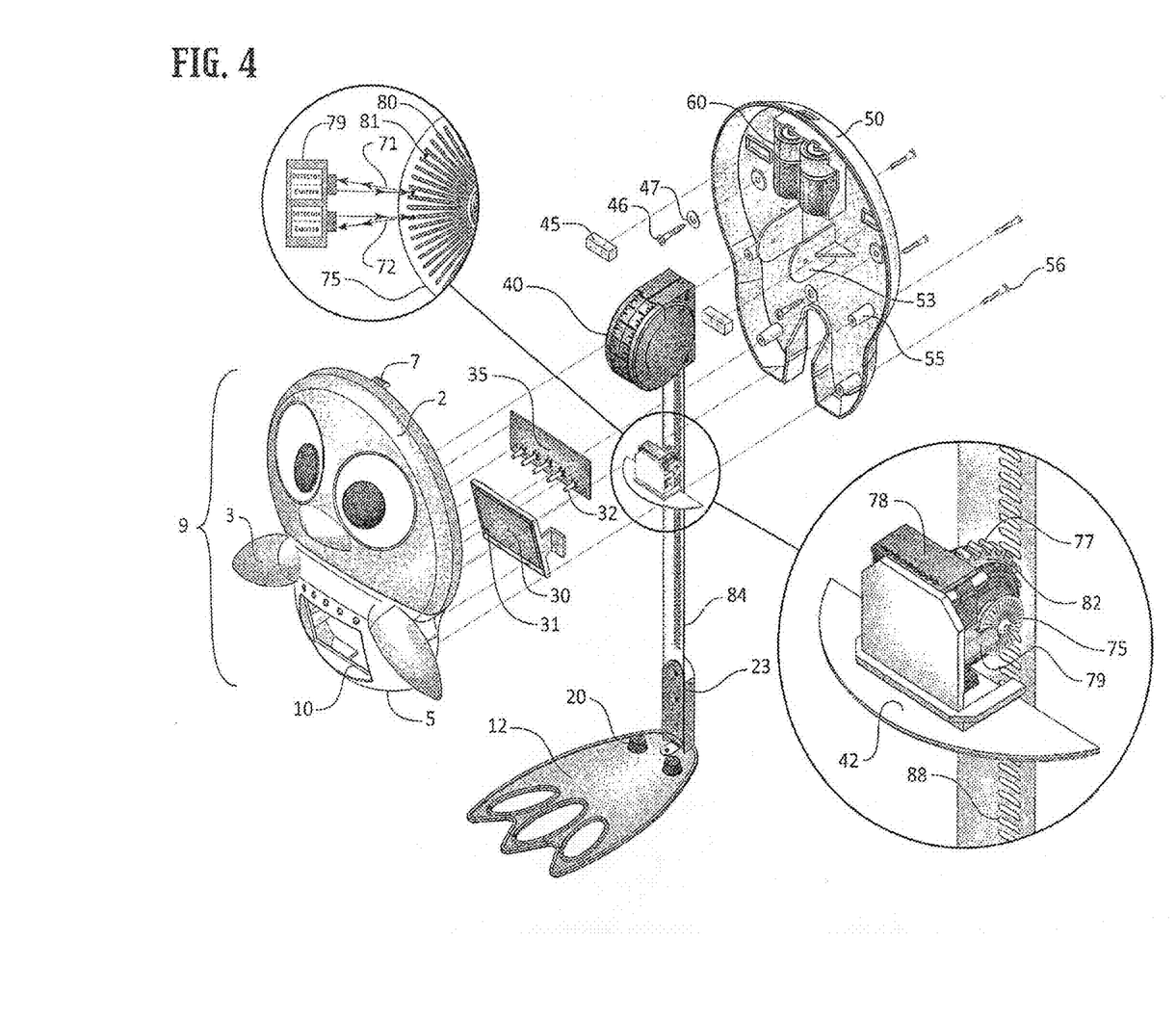
FIG. 4 is an exploded view of the height-measuring device having a rotary encoder sensor.

FIG. 4 depicts an exploded view of the height-measuring device [1] showing rotary encoder [78] embodiment similar in arrangement to the linear encoder [70] embodiment except that a rotary encoder [78] is fixed onto the sensor bracket [42]. The rotary encoder decodes height measurements of users or objects using a set of two coordinated emitter beam ([71], [72]) signals, being 90° out-of-phase, an encoder wheel [75] having a reflective surface, and an array of coded segments [80], which are thin, opaque lines, radially situated around the encoder wheel [75]. Each coded segment [80] is non-reflective and has a certain thickness, and the reflective sectors [81] are spaced equally, radially, and adjacently around the encoder wheel [75] axis. Note that the specificity of number, size, and spacing of these coded segments [80] and reflective sectors [81] determines the rotary encoder's [78] resolution. The encoder module [79], containing the two emitter and detector pairs, is depicted as straddling the encoder wheel's [75] edge, and is fixed adjacently onto the body of the rotary encoder [78]. However, the rotary encoder's [78] actual form factor, dimension, and assembled position may vary.

In operation, the slotted retractable tape [84] travels downward until the adjoined foot platform [12] comes to its final rest atop the user's head or other object. The slotted retractable tape's [84] motion effectively engages, and spins both a drive sprocket [82] and the encoder wheel [75] by means of the slotted retractable tape's [84] array of stamped slots [88] which make interlacing contact with gear teeth

[77] that tangentially circumscribe the drive sprocket [82]. Concurrent to the clockwise, or counterclockwise spinning of the encoder wheel [75], both of the rotary encoder's [78] emitter beams ([71] and [72]) independently fire, and progressively scan circularly around the array of coded segments [80] and reflective sectors [81]. Meanwhile, two respective detectors read, log, and cache the data as two channels of SWPs that are 90° out-of-phase. The first SWP channel is in-phase and may be used for electronic pulse counting, i.e. used in the distance measurement calculation: while the second SWP channel is quadrature and may also be used for counting: but is preferably used in conjunction with the in-phase channel to detect instantaneous direction changes of the encoder wheel [75] which changes in lockstep with the instantaneous direction changes of the slotted retractable tape [84]. Effectively, the electronic pulses are counted and the rotary encoder's [78] algorithm translates these pulse counts into a linear measurement of millimeters per pulse corresponding to the actual travel distance, in millimeters, of the slotted retractable tape [84]. Similar to the linear encoder [70] embodiment, the rotary encoder [78] optionally employs one or both channels, to increment and/or decrement electronic pulse counts; and, it necessarily employs both channels, with quadrature evaluation, to detect encoder wheel [75]/slotted retractable tape [84] direction changes. The foregoing process incrementally aggregates the linear travel distance of the slotted retractable tape [84] and the adjoined foot platform [12]. Technologically, the rotary encoder [78] heretofore mentioned is of the reflective-type but may also be transmissive, given some minor modifications of the apparatus depicted.

Figure 5:
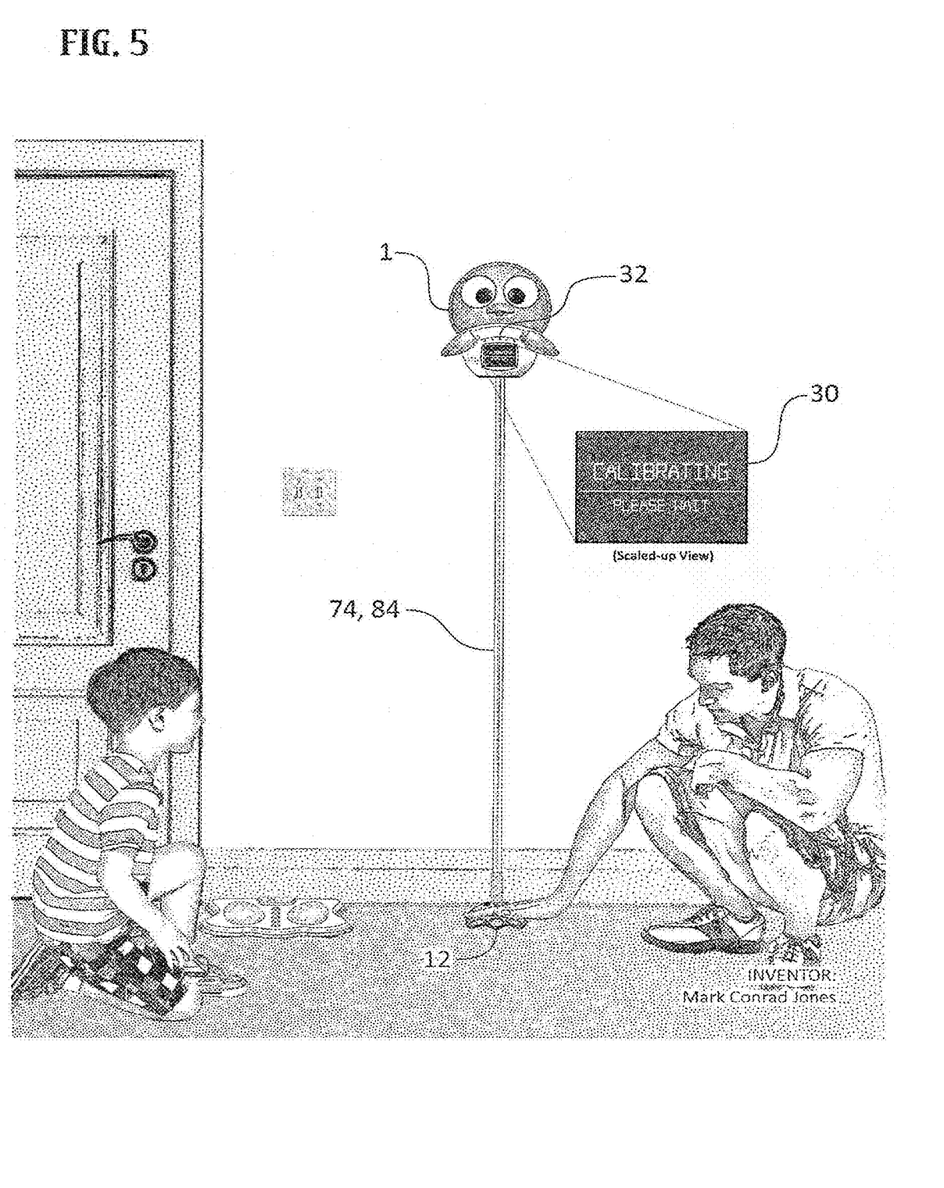
FIG. 5 is an illustrative view of the height-measuring device being calibrated.

FIG. 5 illustrates the calibration process for both the linear encoder [70] and the rotary encoder [78] embodiments. After mounting the height-measuring device [1] onto a wall or other surface, the height-measuring device [1] should be calibrated electronically in order to record its relative position in terms of its distance with respect to the floor. To initiate the as-mounted calibration distance on the height-measuring device [1], the user will initialize calibration either by speaking voice commands, or by depressing one, or more, of the manual pushbutton [32] inputs: or by using GUI inputs on the screen display [30] activated via a touch control interface. Next, the foot platform [12] is either automatically moved or manually pulled downward, allowing the retractable tape [74, 84] to travel, and extend vertically, until the foot platform [12] abuts flat on the floor or other surface. Once the foot platform [12] is held in this static position for a certain period of time, such as 7 seconds, an audible beep may emit, and the calibration distance is instantaneously captured as per the respective embodiment's distance measurement process and algorithm. The calibration reading is stored in memory on the ASIC board [35] and may be displayed on the screen display [30] or alternately an audible signal may be emitted from the height-measuring device's [1] speaker. Once the height-measuring device [1] is calibrated, it is now ready for use by individuals, or objects whose physical height is comfortably less than the calibrated as-mounted distance. No separate individualized calibration is necessary, but the height-measuring device [1] must be recalibrated if the vertical mounting position of height-measuring device changes.

Figure 6:
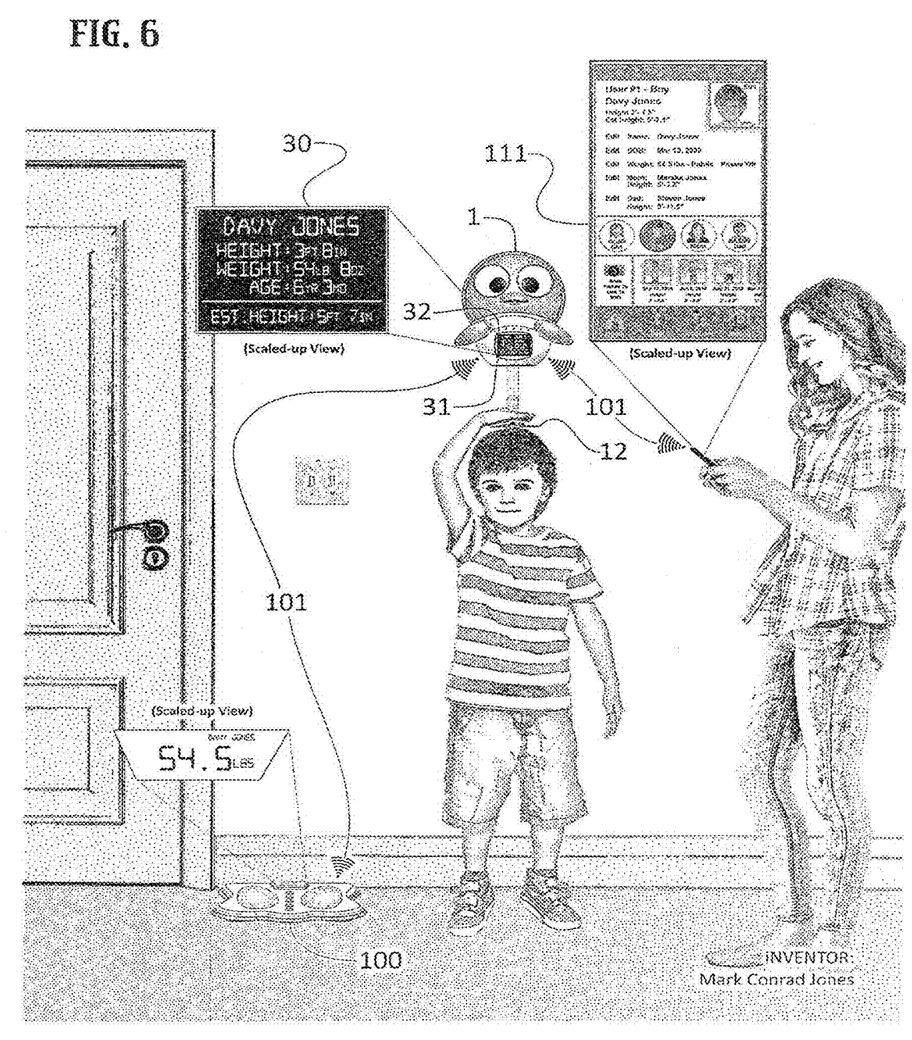
FIG. 6 is an illustrative view of the height-measuring device showing user engagement.

FIG. 6 illustrates the measurement process for a user who is positioned underneath the foot platform [12]. Given a certain setup protocol, the user may first program their personal pushbutton [32], which enables the height-measuring device [1] to recognize who is about to use the device [1], and then permanently correlates the user with the specific programmed pushbutton [32]. Likewise, the user selection of a personalized pushbutton [32] allows height measurements to be added to previously stored personal user data, not limited to previous height, weight, age, name, and gender. Alternately, the user could be automatically recognized via the camera [31] using face recognition software capability.

In operation, the user simply depresses his/her personalized pushbutton [32], and within a certain timeframe, such as 10 seconds. The user pulls the foot platform [12], or it automatically travels downward until it abuts, and rests flatly on the crown of the user's head. Once the foot platform [12] comes to rest on user's head for a predetermined time, such as 3 seconds, an audible beep may emit; and, the respective sensor embodiment, whether linear encoder [70] or rotary encoder [78] will automatically capture, and store in memory, the travel distance of the foot platform [12]. The total user or object height calculation is simply the difference between the stored as-mounted calibration distance, and the actual travel distance of the foot platform [12] as it comes to rest atop its target below. The software algorithm will cache, log, and save the digital height, and this data may be displayed on the screen display [30] and/or played from an audio speaker. Wired or wireless [101] data transmissions from the height measuring device [1] may be shared with a scale [100], a smart phone [111], or any other connected user device. Here, the height-measuring device's screen display [30] is not limited to displaying the user's first and last name, height, weight, age, estimated height, and/or photograph. Likewise, the connected smart phone [111] is not limited to displaying shared data that may include the user's first and last name, current height, estimated future height, DOB, weight, gender, privacy settings, mother's name, mother's height, father's name, father's height, as well as user photographs, that are age, date, and height stamped. And, the connected scale [100] is not limited to displaying the user's name, weight, and the like.

Figure 7:
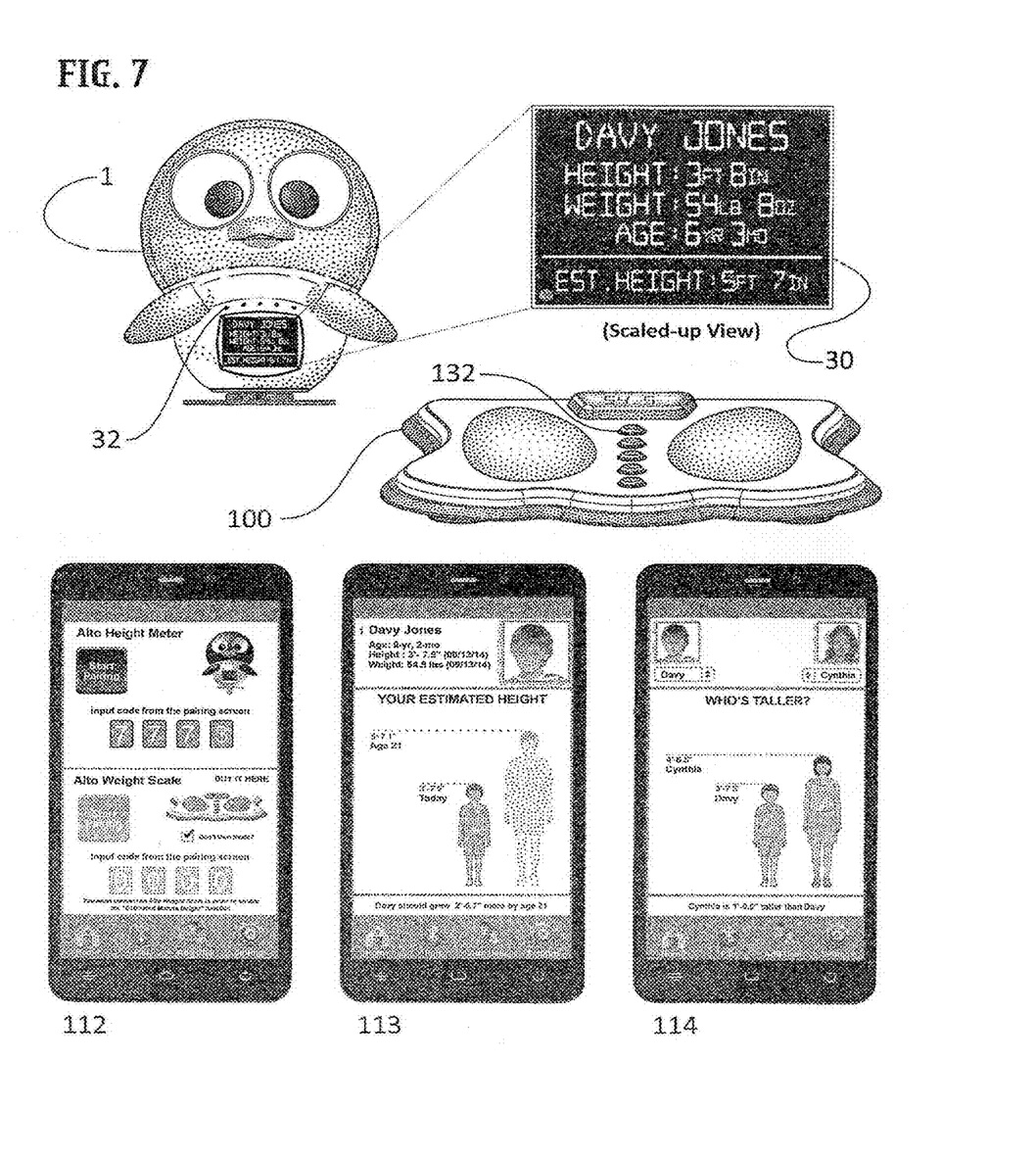
FIG. 7 is an illustrative view of the height-measuring device able to correspond to a smart application and/or scale.

FIG. 7 depicts the preferred system embodiment including the height-measuring device [1] connected to a proprietary weight scale [100] having shared data, memory, and foot-activated pushbuttons [132] corresponding to the height-measuring device's manual pushbuttons [32]. It also depicts smart phones [112], [113], and [114] which represent any number of connected possibilities such as tablets, monitors, personal computers, smart phones, or other devices. Smart phone [113] illustrates a screen, wherein the height-measuring device [1] is calculating, and displaying, a scaled graphical representation of a user's height juxtapose to a figure representing his/her comparative future height. Smart phone [114] illustrates a screen, wherein the height-measuring device [1] is calculating, and displaying, a scaled graphical representation of the user's height juxtapose to a comparative figure of a family member of equal, or different height. Smart phone [112] illustrates a screen in the process of receiving and/or transmitting pairing codes to the height-measuring device [1], and to the weight scale [100] respectively. Once all connected devices have been paired, and information synced and accumulated, the results may be displayed, shared, printed, and/or saved. The general scope of the height-measuring device's [1] data set includes, but is not limited to: personal information, sibling information, parent information, family tree data, medical records, demographic information, and other shared demographic API data.

The description of the disclosure has been presented for purposes of illustration and description, but is not intended to be exhaustive or limited in the form disclosed. It will be apparent to those of skill in the art that many modifications and variations are possible without departing from the scope and spirit of the disclosure, giving full cognizance to equivalents in all respects.

What is claimed:

1. A device for measuring height of a person comprising:
a power supply contained within a housing; said housing having a front shell assembly coupled to a corresponding rear-facing shell configured for mounting onto a stable surface;
said housing having a display aperture with a screen display positioned therein and located adjacent to hardware circuitry having software capable of receiving and storing user input;
a foot platform having an aperture bored therethrough and a tab capable of concealing said aperture;
a retractable tape having two ends, wherein a first end is affixed within said housing and a second end connected to said foot platform by an attachment;
a distance sensor of the linear encoder type which respectively decodes an adjacent retractable tape, and wherein said encoder is comprised of a set of emitter beams and at least one detector, wherein the said emitter beams project onto, and scan over a reflective surface and over an array of non-reflective segments, and wherein said detector reads said signals as the linear tape distance traveled; and
said distance sensor mounted onto a bracket affixed within said housing and capable of determining a height reading of said person; and
wherein said screen display shows said height reading to a user.

2. The device of claim 1, wherein said distance sensor is a rotary encoder, wherein said rotary encoder decodes distance measurements by interpreting rotation of an encoder wheel corresponding to incremental linear distance traveled by said retractable tape.

3. The device of claim 2, wherein said encoder wheel is coaxial with a sprocket having sprocket teeth engaging slots of said retractable tape, causing said sprocket and said encoder wheel to spin in lockstep.

4. The device of claim 1, wherein said screen display is capable of accepting and exhibiting user input thereon and is selected from the group consisting of a touch screen, smartphone, tablet, monitor, camera, speaker, and a scale.

5. The device of claim 1, wherein said hardware circuitry and software are selected from a group consisting of at least one manual pushbutton, processor, wireless radio, memory module, voice recognition module, face recognition module, camera module, microphone, and audio speaker.

6. A method of measuring height of a person, the method comprising:
initiating a height measuring device;
initializing calibration of said height measuring device using an input means;
positioning a foot platform downward by extending a retractable tape to a first position abutting a surface for a predetermined amount of time;
capturing and storing said first position as a calibration reading within encoder hardware and software;
returning said foot platform to its first position by retracting said retractable tape;
repositioning said foot platform in a downward manner to a second position atop said person for a predetermined amount of time;
capturing and storing said second position as a distance reading in said encoder;
Calculating said distance reading from said calibration reading forming a height-measurement reading; and
displaying said height-measurement reading onto a screen display.

7. The method of claim 6, wherein said encoder is selected from a group consisting of a linear encoder and a rotary encoder.

8. The method of claim 6, wherein said initializing calibration by said input means is selected from the group consisting of speaking a voice command, depressing a pushbutton, and using a screen display.

9. A system for measuring height of adult and adolescent users, including the said adolescent user's biological mother and father to additionally facilitate prediction of the heritable future height of said adolescent user, the system comprising:
a processor; and
a non-transitory computer-readable medium coupled to said processor and storing a plurality of instructions, which when executed, cause said processor to handle measurement data, the plurality of instructions comprising:
instructions that cause the processor to determine a height measuring device has initiated;
instructions that cause the processor to determine calibration has initialized;
instructions that cause the processor to determine when a foot platform has moved to a first position on the floor;
instructions that cause the processor to capture and store said first position as a calibration reading;
instructions that cause the processor to determine when said foot platform has moved to a second position;
instructions that cause the processor to capture and store said second position as a distance reading;
instructions that cause the processor to calculate said distance reading from said calibration reading and to determine a resulting height-measurement reading;
instructions that cause the processor to capture and store said resulting height-measurement reading; and
instructions that cause the processor to send said height-measurement reading onto a screen display.

10. The system of claim 9, further comprising instructions that cause the processor to run an algorithm for predicting the heritable future height of said adolescent user, the system comprising:
instructions that cause the processor to retrieve stored data results of said adolescent user; and
instructions that cause the processor to retrieve stored user data results of said adolescent user's said mother and father; and
instructions that cause the processor to utilize said adolescent user data, and the said biological mother and father's user data in order to calculate, and store said heritable future height result of said adolescent user; and
instructions that cause the processor to transmit said heritable future height result of said adolescent user onto said screen display.

11. The system of claim 9, further comprising instructions that cause the processor to determine when a subsequent person initiates said height measuring device, the system comprising:
instructions that cause the processor to determine when said foot platform has moved to a downward position atop said subsequent person;

instructions that cause the processor to capture and store said downward position as a subsequent distance reading;

instructions that cause the processor to calculate said subsequent distance reading from said calibration reading and to determine a resulting height-measurement reading of said subsequent person;

instructions that cause the processor to capture and store said resulting height-measurement reading of said subsequent person; and instructions that cause the processor to display said resulting height-measurement reading of said subsequent person onto a screen display.

12. The system of claim 9, further comprising instructions that cause the processor to compare heights of at least a pair of individuals and store said compared heights; and instructions that cause the processor to display said compared heights onto said screen display.

\* \* \* \* \*